(12) United States Patent
Ye et al.

(10) Patent No.: US 8,987,189 B2
(45) Date of Patent: *Mar. 24, 2015

(54) TREATING HEPATITIS C VIRUS INFECTION

(71) Applicant: Board of Regents, The University of Texas System, Austin, TX (US)

(72) Inventors: Jin Ye, Dallas, TX (US); Fang Sun, Dallas, TX (US); Hua Huang, Dallas, TX (US); Michael J. Gale, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/765,506

(22) Filed: Feb. 12, 2013

(65) Prior Publication Data
US 2014/0056846 A1 Feb. 27, 2014

Related U.S. Application Data

(63) Continuation of application No. 12/631,917, filed on Dec. 7, 2009, now abandoned, which is a continuation of application No. 11/657,856, filed on Jan. 24, 2007, now Pat. No. 7,645,732.

(51) Int. Cl.
*A61K 31/7056* (2006.01)
*A61K 38/21* (2006.01)
*C12N 15/113* (2010.01)
*C12Q 1/02* (2006.01)

(52) U.S. Cl.
CPC ........... *C12Q 1/025* (2013.01); *A61K 38/21* (2013.01); *C12N 15/113* (2013.01); *C12N 2310/14* (2013.01); *C12N 2770/24211* (2013.01); *A61K 31/7056* (2013.01)
USPC .......................................................... 514/1

(58) Field of Classification Search
None
See application file for complete search history.

(56) References Cited

U.S. PATENT DOCUMENTS

2010/0310553 A1 * 12/2010 Luo ........................... 424/133.1

FOREIGN PATENT DOCUMENTS

WO WO 2008021353 * 12/2007

* cited by examiner

*Primary Examiner* — Sean McGarry
(74) *Attorney, Agent, or Firm* — Richard Aron Osman

(57) ABSTRACT

Methods and compositions are provided to inhibit release of HCV from an HCV-infected cell by contacting the cell with a VLDL assembly inhibitor, and detecting a resultant inhibition of HCV release from the cell. The methods can be used to decrease serum viremia of an HCV-infected person.

20 Claims, No Drawings

TREATING HEPATITIS C VIRUS INFECTION

This application is a continuation of Ser. No. 12/631,917, filed: Dec. 7, 2009, which is a continuation of Ser. No. 11/657,856 filed Jan. 24, 2007.

This work was supported by National Institute of Health Grant No. 5 P01 HL20948-30 titled Molecular Basis of Cholesterol Metabolism. The U.S. government has rights in any patent issuing on this application.

BACKGROUND OF THE INVENTION

Many viruses can be produced in large amount only in certain specialized cell types. A classic example is hepatitis C virus (HCV), a single stranded positive RNA virus of the Flaviviridae family (Appel et al., 2006), that can be secreted abundantly only by hepatocytes (Chisari, 2005). The factors responsible for this restriction are largely unknown. In the case of HCV, one clue derives from the demonstration that at least a portion of HCV circulates in plasma in complex with Very Low Density Lipoproteins (VLDL) (Andre et al., 2002; Nielsen et al., 2006), a family of spherical particles that are produced only in liver (Gibbons et al., 2004) to export triglyceride and cholesterol ester into plasma (Gibbons et al., 2000). Although HCV and VLDL circulate together, a role for VLDL in viral assembly or secretion has never been demonstrated.

As for all positive-strand RNA viruses, HCV RNA replication occurs in association with cytoplasmic membranes. In the case of HCV these structures, called 'membranous webs', have been visualized in cultured human hepatoma Huh7 cells that harbor a subgenomic replicon of HCV (Gosert et al., 2003; Moradpour et al., 2004). These replicons are engineered HCV RNA molecules that contain essential elements for RNA replication, including the coding sequence for the nonstructural (NS) proteins NS3, NS4A, NS4B, NS5A and NS5B (Lohmann et al., 1999). After transfection into Huh7 cells, the replicon RNA replicates but it does not produce infectious viral particles because it does not encode the structural proteins that are required for assembly and secretion of the virus (Lohmann et al., 1999). The membranous webs that harbor the HCV replication complex have never been isolated and their composition is unknown.

VLDL assembly is currently believed to occur at two different stages (Shelness and Sellers, 2001). In the first stage, Microsomal triglyceride transfer protein (MTP) transfers lipid to nascent apolipoprotein B, a huge 540 Kda protein that gives structural integrity of VLDL (Olofsson and Boren, 2005). Without sufficient lipid binding, apoB becomes ubiquitinated and degraded during translation (Avramoglu and Adeli, 2004). The apoB-containing lipid particles produced in the first stage of VLDL assembly contain only limited amounts of triglyceride (Gusarova et al., 2003). In the second stage, apoB-containing precursor particles are fused with triglyceride droplets in the luminal compartment (Shelness and Sellers, 2001), a step probably facilitated by apolipoprotein E (apoE), another major protein component in VLDL (Mensenkamp et al., 2001). Although not essential for the direct fusion event, MTP is required to transfer triglyceride from the cytosol to the luminal compartment (Shelness and Sellers, 2001). In human and mice, a genetic defect in MTP severely reduces VLDL secretion (Sharp et al., 1993; Raabe et al., 1998). While the first stage of VLDL assembly is known to occur at the endoplasmic reticulum (ER) (Gusarova et al., 2003), the exact location of the second stage remains controversial (Fisher and Ginsberg, 2002).

SUMMARY OF THE INVENTION

In one aspect, the invention is a method of inhibiting release of HCV from an HCV-infected cell, the method comprising: a) contacting the cell with a VLDL assembly inhibitor; and b) detecting a resultant inhibition of HCV release from the cell. In a particular embodiment, the cell is contacted with a submicromolar amount of the inhibitor. In various embodiments, the inhibitor is an MTP inhibitor or a small interfering RNA or antisense oligonucleotide directed against apolipoprotein B. In particular embodiments, the contacting step further comprises contacting the cell with an antiviral agent selected from interferon and ribavirin.

In another aspect, the invention is a method of decreasing serum viremia of an HCV-infected person, the method comprising: a) administering to the person a VLDL assembly inhibitor; and b) detecting a resultant decrease in serum viremia in the person. In a particular embodiment, the decrease in serum viremia is effected by a submicromolar concentration of the VLDL assembly inhibitor, such as an MTP inhibitor. In various other embodiments, the inhibitor is an MTP inhibitor selected from the group consisting of BMS-200150, BMS-212122, BMS-201038 (AERG-733), BMS-201030, BMS-197636, JTT-130, mitratapide (R-103757), implitapide (BAY-139952), CP-346086, CP-467688, and CP-319340. In another embodiment the inhibitor is a small interfering RNA or antisense oligonucleotide, such as ISIS 301012, directed against apolipoprotein B. In particular embodiments, the contacting step further comprises contacting the cell with an antiviral agent selected from interferon and ribavirin.

Another aspect of the invention is a kit for decreasing serum viremia of an HCV-infected person, the kit comprising: a) a plurality of MTP-inhibitor dosage forms; and a) a plurality of ribavirin dosage forms. In specific embodiments, the MTP-inhibitor is selected from the group consisting of BMS-200150, BMS-212122, BMS-201038 (AERG-733), BMS-201030, BMS-197636, JTT-130, mitratapide (R-103757), implitapide (BAY-139952), CP-346086, CP-467688, and CP-319340.

DETAILED DESCRIPTION OF SPECIFIC EMBODIMENTS OF THE INVENTION

We describe a method of inhibiting release of hepatitis C virus (HCV) from an HCV-infected cell, the method comprising: a) contacting the cell with a VLDL assembly inhibitor; and b) detecting a resultant inhibition of HCV release from the cell.

The VLDL assembly inhibitor preferably blocks the assembly and secretion of VLDL by inhibiting the activity of MTP or limiting the production of apoB protein.

In one embodiment, the VLDL assembly inhibitor is a small interfering RNA or antisense oligonucleotide directed against apoB. As one example, ISIS 301012 is an antisense oligonucleotide in clinical development that targets human ApoB-100 (Burnett, Curr Opin Mol Ther. (2006) 8:461-7).

In particular embodiments, the VLDL assembly inhibitor is a molecule that binds to and inhibits MTP activity, and is preferably a synthetic (i.e. non-naturally occurring) molecule that inhibits MTP activity at submicromolar concentrations. Synthetic MTP inhibitors are well-known in the art such as BMS-200150 (see e.g. Jamil et al, Proc Natl Acad Sci USA. (1996) 93:11991-5), BMS-212122 (see e.g. Robl et al, J Med Chem. (2001) 44:851-6), BMS-201038 (under development as AERG-733; see e.g. Sulsky et al, Bioorg Med Chem Lett. (2004) 14:5067-70), BMS-197636 (see e.g. Wang et al, J Biol Chem (1999) 274:27793-800), JTT-130 (see e.g. Aggarwal et al, BMC Cardiovasc Disord (2005) 5:30; and Burnett, IDrugs (2006) 9:495-9), mitratapide (also known as R-103757; see e.g. Verreck et al, J Pharm Sci (2004) 93:1217-28), implitapide (also known as BAY-139952; see e.g. Ueshima et al, Biol Pharm Bull (2005) 28:247-52), CP-346086 (see e.g. Chandler et al, J Lipid Res. (2003) 44:1887-901), CP-467688 and CP-319340 (see e.g. U.S. Pat. No. 5,919,795), and others.

The invention encompasses methods useful for screening VLDL assembly inhibitors for their inhibition of HCV release from a cell, which may be in vitro or in situ in chimpanzee, an animal model for HCV infection. In these embodiments, the contacting step is effected using any method suitable to achieve uptake of the VLDL assembly inhibitor by the cell. For example, siRNA can be transfected into the cells in vitro with OligofectAMINE™ reagent (Invitrogen). Small molecule inhibitors, such as the above-mentioned MTP inhibitors, can be simply added to the medium of cells in culture. Additional MTP inhibitors for use in the method can be identified using an MTP inhibition assay (see e.g. Chandler et al, J Lipid Res. (2003) 44:1887-901), and optionally further validated in chimpanzee. In a particular embodiment, the cell is contacted with a submicromolar amount of the VLDL assembly inhibitor. For example, the cell may be in a culture medium to which is added an amount of the VLDL assembly inhibitor to achieve a concentration in the medium of less than 1000 nM, and preferably less than 500, 250, 100 or 10 nM. A resultant inhibition of HCV release is detected using any suitable method, such as the HCV release assay described in Example 2. The method can be used to assess the additive or synergistic effects a VLDL assembly inhibitor has with other antiviral agents such as ribavirin and/or interferon. Accordingly, the contacting step of the method may further comprise contacting the cell with an antiviral agent selected from interferon and/or ribavirin.

The invention encompasses methods to decrease serum viremia in an HCV-infected person, the method comprising: a) administering to the person a VLDL assembly inhibitor; and b) detecting a resultant decrease in serum viremia in the person. Prior to the contacting step, the patient is preferably diagnosed as having an HCV infection, which may be by any medically-acceptable method. The VLDL assembly inhibitor may be a known drug used in or in development for treatment of hyperlipidemia.

Applicable protocols for administering a VLDL assembly inhibitor to a person are known in the art and routinely optimized. For example, the antisense oligonucleotide ISIS 301012 demonstrates bioavailability by oral and parental routes of administration (Isis Pharmaceuticals 2005 Annual Report). Small molecule MTP inhibitors are routinely administered in oral dosage forms. Suitable protocols for administration of the VLDL assembly inhibitor to a patient can be readily derived from the extensive clinical trials and preclinical pharmacokinetic studies that have been conducted on VLDL assembly inhibitors for the treatment of hyperlipidemia.

In a preferred embodiment, a submicromolar serum concentration of the VLDL assembly inhibitor, particularly an MTP inhibitor, effects the decrease in serum viremia. In a particular embodiment, 1 mg per kilogram of body weight per day or less of the MTP inhibitor is administered to the person to achieve an active submicromolar concentration of the inhibitor for a duration sufficient to decrease serum viremia in the patient. For example, the MTP inhibitor may be formulated in oral dosage forms of 0.03, 0.1, 0.3 and 1.0 mg per kilogram of body weight per day, delivered 1-4 times daily to achieve a submicromolar serum concentration of the MTP inhibitor. The duration of treatment is typically in the range of about 4 weeks-4 months, depending on the tolerance of the drugs by patients. The resultant decrease in serum viremia may be detected quantitatively using a suitable method known in the art (see e.g. Lunel et al, Hepatology (1999) 29:528-35). In a particular embodiment, a resultant decrease in serum viremia is detected by demonstrating a significant decrease in serum HCV RNA titer (e.g. using NASBA® test, Organon Teknika, Boxtel, The Netherlands) compared to pre-treatment titer. In particular embodiments, the method results in at least a 25%, 50%, 75%, 80%, or greater decrease in serum HCV RNA titer. In other embodiments, a decrease in serum viremia is detected inferentially, for example by observing a reduction of HCV symptoms in the patient, or indirectly, such as by showing an improvement in some other indicator of HCV infection (e.g. normalization of aminotransferase levels compared to pre-treatment levels).

The invention provides combination therapies for treating HCV infection in a person comprising administering the patient a VLDL assembly inhibitor in combination with one or more additional antiviral agents that act by a mechanism other than by VLDL assembly inhibition. In a particular embodiment, the VLDL assembly inhibitor targets and inhibits activity of MTP or production of ApoB protein, and the additional antiviral agent is interferon and/or ribavirin. Kits for decreasing serum viremia of an HCV-infected person can comprise the combined antiviral agents. For example, in one embodiment, the kit comprises a plurality of VLDL assembly inhibitor dosage forms, preferably orally administered capsules or tablets, and a plurality of ribavirin dosage forms. Alternatively the two or more antiviral agents may be formulated in a single dosage form. The kit may comprise the dosage forms packaged in a blister pack to facilitate proper daily dosing. In a specific embodiment, the kit comprises a plurality of MTP-inhibitor dosage forms wherein the MTP-inhibitor is selected from the group consisting of BMS-200150, BMS-212122, BMS-201038 (AERG-733), BMS-197636, JTT-130, mitratapide (R-103757), implitapide (BAY-139952), CP-346086, CP-467688, and CP-319340. The kit further comprises a plurality of orally administrable ribavirin and/or interferon (see e.g. Bernard, Curr Opin Investig Drugs (2002) 3:693-7) dosage forms.

Example 1

Decreased Secretion of Infectious HCV Particles from Cells Treated with siRNA Targeting apoB We transfected Huh7-GL cells, a line of Huh7 cells that contain a chromosomally integrated genotype 2a HCV cDNA and constitutively produce infectious virus (Cai et al., 2005), with a duplex siRNA targeting apoB or GFP as a control. Following incubation in serum-free medium, culture medium was harvested and the amount of apoB and HCV in the medium was analyzed. Transfection of cells with the apoB siRNA reduced the amount of apoB mRNA by about 80% without affecting intracellular HCV RNA. The apoB siRNA markedly decreased the amount of apoB secreted into the medium, but it did not affect secretion of α1-antitrypsin. In control cells transfected with the GFP siRNA, the HCV copy number and titer increased by more than 10 fold during the period of 4-hr incubation. In cells receiving the apoB siRNA, this increase was reduced by about 50% as assayed by viral copy number, and 70% as assayed by the viral titer.

Example 2

Decreased Secretion of Infectious HCV Particles from Cells Treated with the MTP Inhibitor BMS-2101038

Huh7-GL cells were incubated in the absence or presence of the MTP inhibitor BMS-210138. Following incubation in serum-free medium, culture medium was harvested and the amount of HCV RNA, HCV titer, and apoB in the medium was measured. Incubation of cells with the MTP inhibitor blocked the secretion of apoB but not α1-antitrypsin. Treatment of the cells with the MTP inhibitor reduced the amount of HCV RNA in the medium and viral titer by about 80%. The decreased amount of HCV in the medium is not due to inhibition of HCV RNA synthesis because intracellular HCV RNA remained the same in the absence or presence of the MTP inhibitor. We did not observe an accumulation of intracellular HCV RNA in cells treated with the MTP inhibitor because even in cells that were not incubated with the inhibitor, the amount of HCV RNA detected in the medium was less than 1% of that found in cells Example 3

Various MTP Inhibitors Decrease Cellular Release of HCV

Huh7-GL cells are cultured as described in Example 2. On day 1, the cells are treated with 1 nM, 10 nM, 100 nM, and 500 nM of the following MTP inhibitors: BMS-201038 (positive control), BMS-200150, BMS-212122, BMS-197636, JTT-130, Implitapide, mitratapide, and CP-346086. 16 hr later on day 2, cells are switched to serum-free medium in the absence or presence of the same amount of the MTP inhibitor. After incubation for 4 hours, decreases in cellular release of virus for each tested inhibitor is demonstrated by reductions in HCV RNA copy numbers and titers in the media as determined above.

Example 4

MTP Inhibitors Decrease Serum HCV Viremia

A randomized, double-blind, placebo-controlled trial (Raymond et al, Ann Intern Med. Nov. 15, 1998; 129(10): 797-800) is used to evaluate the efficacy and safety of BMS201038 in patients with chronic HCV infection who did not respond to or were intolerant of interferon monotherapy.

Patients are recruited and are eligible for enrollment if they are positive for HCV RNA on serologic testing after at least 3 months of interferon therapy. Patients who can not tolerate interferon because of severe side effects, such as fatigue, neuropsychiatric disturbances, or thrombocytopenia, are also included. Patients are excluded if they are taking lipid-lowering medications, are pregnant, are currently abusing drugs or alcohol, have hepatoma, are seropositive for HIV, have an absolute granulocyte count less than 1000 cells/mm3, or have a coexistent cause of liver disease.

Patients are randomly assigned in a double-blinded manner to receive a 12-week course of either BMS201038 at 0.15 mg per kilogram of bodyweight twice daily or a placebo that is identical in shape, color, and packaging to the active drug. Physicians and patients are blinded to treatment assignments. Patients are evaluated every 3 weeks for compliance, which is assessed by pill count, and for the development of adverse reactions. Adverse reactions are not expected at these doses and the duration of the treatment given the high tolerability of BMS-201038 as demonstrated in previous clinical trials (see e.g. Cuchel et al, N. Eng. J Med (2007) 356:148-56). At each evaluation visit, a complete blood count is done and serum levels of electrolytes, blood urea nitrogen, creatinine, aspartate aminotransferase, alanine aminotransferase, albumin, and total bilirubin are measured. Titers of serum HCV RNA are assessed before enrollment, at each evaluation visit, and 6 weeks after the final dose by using a qualitative multicycle reverse transcription polymerase chain reaction method. Titers are calculated up to 5 million copies/mL; if a titer is greater than 5 million copies/mL, it is simply reported as such and the exact value is not given. Efficacy of BMS-201038 is demonstrated by a decrease in serum viremia as demonstrated by a significant decrease in viral load and normalization of elevated aminotransferase levels.

References cited above are incorporated herein by reference for their disclosure of the structures and synthesis of the VLDL assembly inhibitors referenced therein.

REFERENCES

Appel, N., et al. (2006) J. Biol. Chem. 281, 9833-9836.
Avramoglu, R. K. and Adeli, K. (2004) Rev. Endocr. Metab. Disord. 5, 293-301.
Cai, Z., et al. (2005) J. Virol. 79, 13963-13973.
Chandler, C. E., et al. (2003) J. Lipid Res. 44, 1887-1901.
Chisari, F. V. (2005) Nature 436, 930-932.
Fisher, E. A. and Ginsberg, H. N. (2002) J. Biol. Chem. 277, 17377-17380.
Gibbons, G. F., et al. (2004) Biochem. soc. trans. 32, 59-64.
Gibbons, G. F., et al. (2000) Biochimica et Biophysica Acta (BBA)—Molecular and Cell Biology of Lipids 1483, 37-57.
Gosert, R., et al. (2003) J. Virol. 77, 5487-5492.
Gusarova, V., et al. (2003) J. Biol. Chem. 278, 48051-48058.
Higashi, Y., et al. (2003) J. Biol. Chem. 278, 21450-21458.
Lohmann, V., et al. (1999) Science 285, 110-113.
Mensenkamp, A. R., et al. (2001) E. Journal of Hepatology 35, 816-822.
Moradpour, D., et al. (2004). J. Virol. 78, 7400-7409.
Nielsen, S. U., et al. (2006) J. Virol. 80, 2418-2428.
Olofsson, S. O. and Boren, J. (2005) J. of Internal Medicine 258, 395-410.
Raabe, M., et al (1998) Proc. Natl. Acad. Sci. 95, 8686-8691.
Randhawa, et al. (2000) Mol. Biol. Cell 11, 2403-2417.
Rowe, T., et al (1996) J. Cell Biol. 135, 895-911.
Sharp, D., et al. (1993) Nature 365, 65-69.
Wetteraue, J. R. al (1998) Science 282, 751-754.

What is claimed is:

1. A method of decreasing serum viremia of an hepatitis C virus (HCV)-infected person, the method comprising the step of administering to the person an effective amount of lomitapide (BMS-201038; N-(2,2,2-trifluoroethyl)-9-[4-[4-[[[4'-(trifluoromethyl)[1,1'-biphenyl]2-yl]carbonyl]amino]-1-piperidinyl]butyl]9H-fluoren-9-carboxamde), wherein a resultant decrease in the serum viremia is effected by a submicromolar concentration of the lomitapide.

2. The method of claim 1 wherein the administering step comprises delivering to the person 1 mg/kg body weight per day or less of the lomitapide for a duration sufficient to decrease the viremia.

3. The method of claim 1 wherein the administering step comprises delivering to the person 0.1 mg/kg body weight per day or less of the lomitapide for a duration sufficient to decrease the viremia.

4. The method of claim 1 further comprising the step of detecting a resultant decrease in serum viremia in the person.

5. The method of claim 1 wherein the administering step comprises delivering to the person 0.1 mg/kg body weight per day or less of the lomitapide for a duration sufficient to decrease the viremia, further comprising the step of detecting a resultant decrease in serum viremia in the person.

6. The method of claim 1 wherein the administering step further comprises administering to the person an antiviral agent selected from interferon and ribavirin.

7. The method of claim 1, wherein the person is determined to be nonresponsive to interferon monotherapy.

8. The method of claim 1, wherein the person is positive for HCV after at least 3 months of interferon therapy.

9. The method of claim 1 wherein the administering comprises delivering to the person 0.1 mg/kg body weight per day or less of the lomitapide for a duration sufficient to decrease the viremia, further comprising the step of detecting a resultant decrease in serum viremia in the person, the administering step further comprises administering to the person an antiviral agent selected from interferon and ribavirin, and the person is positive for HCV after at least 3 months of interferon therapy.

10. A method of treating a hepatitis C virus (HCV) infection in a person determined to be HCV-infected, comprising the step of administering to the person lomitapide (BMS-201038; N-(2,2,2-trifluoroethyl)-9-[4-[4-[[[4'-(trifluoromethyl)[1,1'-biphenyl]2-yl]carbonyl]amino]-1-piperidinyl]butyl]9H-fluoren-9-carboxamde), wherein a resultant decrease in the serum viremia is effected by a submicromolar concentration of the lomitapide.

11. The method of claim 10, wherein the patient is determined to be nonresponsive to interferon monotherapy.

12. The method of claim 10, wherein the patient is positive for HCV after at least 3 months of interferon therapy.

13. The method of claim 10 wherein the administering step comprises delivering to the person 1 mg/kg body weight per day or less of the lomitapide for a duration sufficient to decrease the viremia.

14. The method of claim 10 wherein the administering step comprises delivering to the person 0.1 mg/kg body weight per day or less of the lomitapide for a duration sufficient to decrease the viremia.

15. The method of claim 10 further comprising the step of detecting a resultant decrease in serum viremia in the person.

16. The method of claim 10 wherein the administering step comprises delivering to the person 0.1 mg/kg body weight per day or less of the lomitapide for a duration sufficient to decrease the viremia, further comprising the step of detecting a resultant decrease in serum viremia in the person.

17. The method of claim 10 wherein the administering step further comprises administering to the person an antiviral agent selected from interferon and ribavirin.

18. The method of claim 10 wherein the administering comprises delivering to the person 0.1 mg/kg body weight per day or less of the lomitapide for a duration sufficient to decrease the viremia, further comprising the step of detecting a resultant decrease in serum viremia in the person, the administering step further comprises administering to the person an antiviral agent selected from interferon and ribavirin, and the person is positive for HCV after at least 3 months of interferon therapy.

19. The method claim 1 wherein the submicromolar concentration is less than 100 nM.

20. The method claim 10 wherein the submicromolar concentration is less than 100 nM.

* * * * *